United States Patent [19]

Byrd

[11] Patent Number: 5,704,916
[45] Date of Patent: Jan. 6, 1998

[54] OXYGEN TUBE SUPPORT APPARATUS AND ASSOCIATED METHOD

[76] Inventor: Timothy N. Byrd, 1267 Old Cades Cove Rd., Townsend, Tenn. 37882

[21] Appl. No.: 565,759

[22] Filed: Nov. 30, 1995

[51] Int. Cl.$^6$ ................................................ A61M 5/32
[52] U.S. Cl. .................... 604/179; 128/DIG. 26; 128/207.17; 604/174
[58] Field of Search .................. 604/174, 175, 604/179, 180; 128/207.12, 207.13, 207.17, 207.18, DIG. 26

[56] References Cited

U.S. PATENT DOCUMENTS

| | | |
|---|---|---|
| 3,370,818 | 2/1968 | Perr . |
| 4,012,544 | 3/1977 | Richards . |
| 4,018,221 | 4/1977 | Rennie . |
| 4,336,806 | 6/1982 | Eldridge, Jr. ................ 128/348 |
| 4,569,348 | 2/1986 | Hasslinger . |
| 4,665,566 | 5/1987 | Garrow ........................ 128/207.18 |
| 4,739,757 | 4/1988 | Edwards ...................... 128/207.18 |
| 4,774,946 | 10/1988 | Ackerman .................... 128/207.18 |
| 4,836,200 | 6/1989 | Clark ........................... 128/207.18 |
| 5,368,024 | 11/1994 | Jones ............................ 128/207.17 |

Primary Examiner—Sam Rimell
Assistant Examiner—Luke J. Yeh
Attorney, Agent, or Firm—Michael E. McKee

[57] ABSTRACT

An apparatus and method for supporting a nasal cannula having two branches across the face of a patient for use utilizes a strap positionable across the top of the head of a patient wherein the strap includes two opposite end portions which are disposed adjacent the ears of the patient when the strap is positioned across the head. An amount of adhesive is borne by each end portion of the strap for adhesively securing the branches of the nasal cannula to the end portions of the strap so that by adhesively securing each of the two branches to a corresponding end portion of the strap and then positioning the strap across the head of a patient, the branches are suspended across the patient's head by the strap and prevented from shifting relative to the end portions by the adhesive.

16 Claims, 2 Drawing Sheets

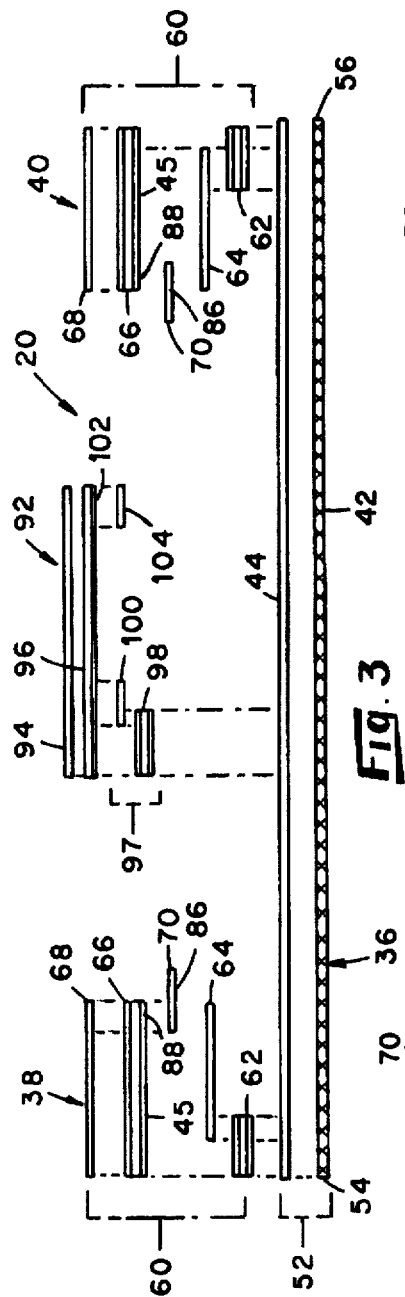
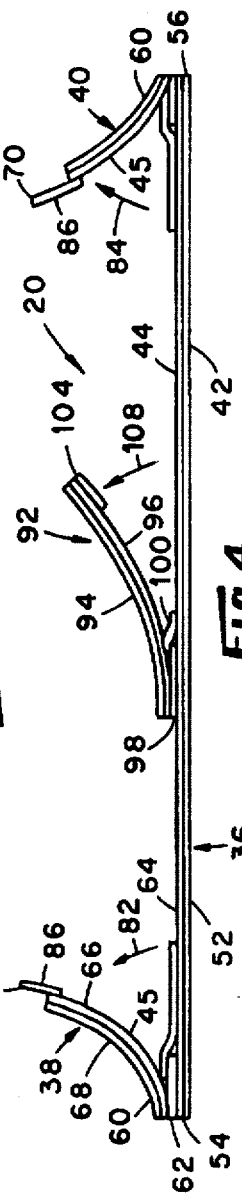
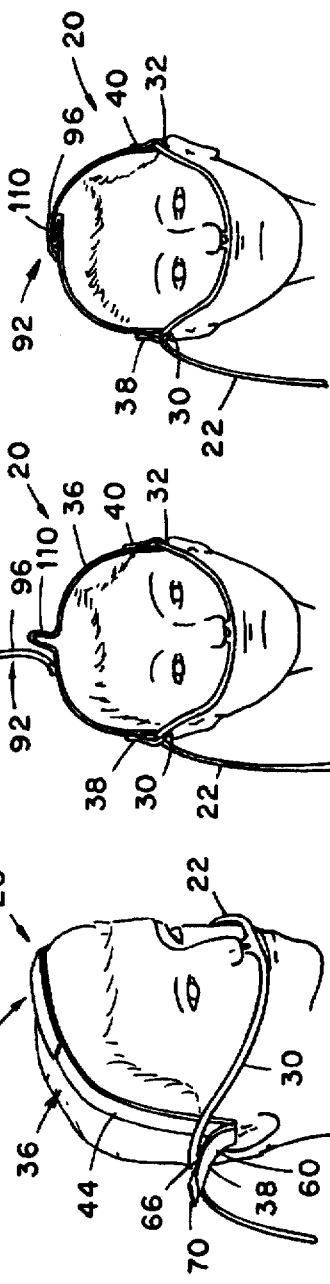

OXYGEN TUBE SUPPORT APPARATUS AND ASSOCIATED METHOD

BACKGROUND OF THE INVENTION

This invention relates generally to the delivery of oxygen to a patient by way of an oxygen nasal cannula and relates, more particularly, to the means and methods by which such a cannula is held in position adjacent a patient's face and nostrils for use.

Nasal cannula commonly comprise an oxygen-carrying tube having two branches capable of being draped over the ears of a patient and which are joined together in front of the patient's face with a central portion providing two nostril orifices. In order that the orifices of the cannula remain in registry with the patient's nostrils during use, the branches of the cannula are typically draped across and supported by the patient's ears so that the branches function as earpieces for holding the cannula in place. It is known, however, that the contact between the cannula branches and the patient's ears may cause irritation and related discomfort in the region above and behind the patient's ears.

In order to prevent such irritation and promote the comfort of the patient while the cannula is being used, the cannula can be held in place across the patient's face while the branches are supported across the top of the patient's head by known apparatus and maintained in a spaced relationship with the patient's ears. For example, U.S. Pat. No. 4,836,200 describes a strap-like device adapted to be draped across the top of a patient's head and which has two looped end portions through which the branches of the cannula are routed. If the length of the strap-like device is sized appropriately, the branches will be suspended in a spaced relationship above the patient's ears as the strap-like device is draped across the patient's head. By supporting the branches above the patient's ears in this manner, the likelihood that the cannula will irritate or cause discomfort to the patient is appreciably reduced.

However, strap-like devices such as those described in the referenced patent are limited in that when the branches are supported within the end portions of the strap-like device, the branch portions may shift in position (i.e. in a lengthwise direction) relative to the end portion of the device. Of course, if the branches are inadvertently shifted relative to the end portions in this manner, the nostril orifices may move out of registry with the patient's nostrils and render the cannula ineffective for its intended purpose and uncomfortable to the patient.

It is an object of the present invention to provide a new and improved strap-like apparatus of the aforedescribed class for supporting the branches of a nasal cannula on opposite sides of a patient's head and in a spaced relationship with the patient's ears and a method of attaching the cannula to the apparatus.

Another object of the present invention is to provide such an apparatus wherein the branches of a nasal cannula supported thereby are prevented from shifting relative to the apparatus.

Still another object of the present invention is to provide such an apparatus which can be readily adjusted in size so that a single apparatus can be suitably draped across a head within a range of head sizes for supporting a nasal cannula thereacross.

Yet another object of the present invention is to provide such an apparatus which is uncomplicated in construction, economical to manufacture, and effective in operation.

SUMMARY OF THE INVENTION

This invention resides in apparatus and an associated method for supporting a nasal cannula across the face of a patient for use wherein the nasal cannula includes two branches positionable on opposite sides of the patient's head when the cannula is used.

The apparatus of the invention includes strap means positionable across the head of a patient, and the strap means includes two opposite end portions which are disposed adjacent the ears of the patient when the strap means are positioned across the head as aforesaid. An amount of adhesive is borne by each end portion of the strap means for adhesively securing each branch of the nasal cannula to a corresponding end portion of the strap means so that by adhesively securing each branch to a corresponding end portion of the strap means and positioning the strap means across the head of a patient as aforesaid, the branches of the nasal cannula are supported on opposite sides of the patient's head by the strap means and prevented from shifting relative to the end portions by the adhesive borne thereby.

The method of the invention includes the steps involved in attaching a nasal cannula to the apparatus of the invention. Such steps include the providing of the strap means, and adhesively securing each branch of the nasal cannula to a corresponding end portion of the strap means so that by adhesively securing each branch to a corresponding end portion of the strap means and positioning the strap means across the head of a patient, the branches of the nasal cannula are supported on opposite sides of the patient's head by the strap means and prevented from shifting relative to the end portions.

BRIEF DESCRIPTION OF THE DRAWINGS

FIG. 3 is a side elevational view of the FIG. 1 apparatus, shown exploded.

FIG. 4 is a side elevational view of the FIG. 1 apparatus, shown assembled and having portions peeled back from the remainder thereof.

FIG. 5 is a perspective view of the FIG. 1 apparatus shown in the process of being attached to a nasal cannula for use.

FIGS. 6 and 7 are views of the FIG. 1 apparatus and the head of a patient illustrating in sequence the steps involved in adjusting the length of the apparatus so that the branches of the cannula are supported by the apparatus in spaced relationship with the patient's ears.

DETAILED DESCRIPTION OF THE ILLUSTRATIVE EMBODIMENTS

Figure 1:
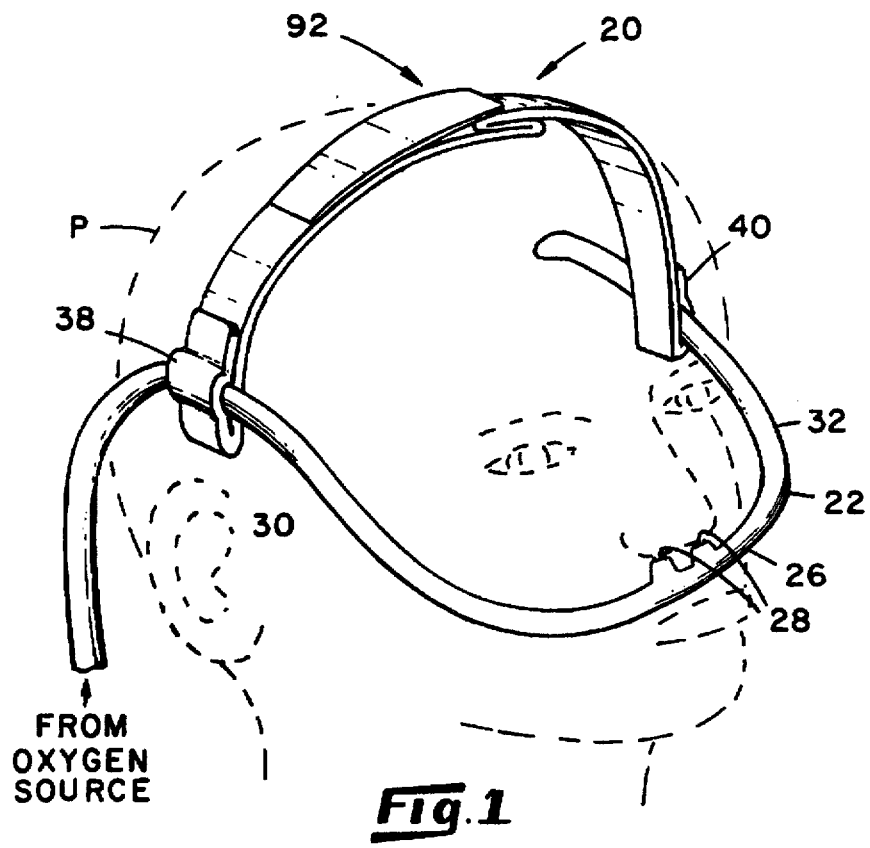
FIG. 1 is a perspective view of an embodiment of an apparatus shown supporting a nasal cannula about the head of a patient for use.
Figure 2:
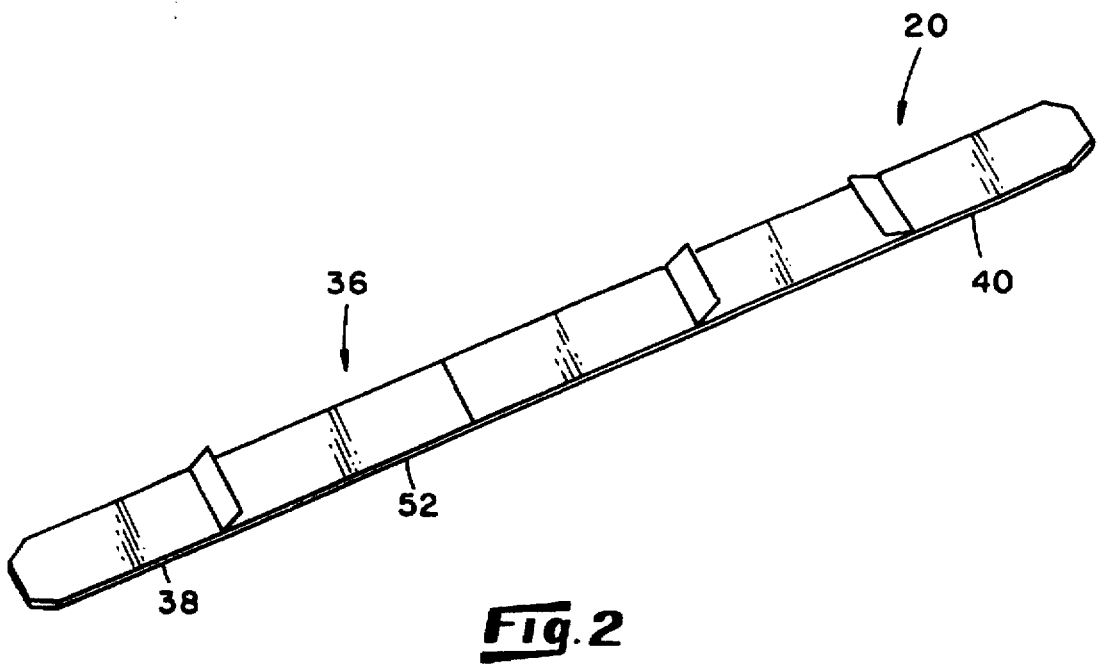
FIG. 2 is a perspective view of the FIG. 1 apparatus, shown before use.

Turning now to the drawings in greater detail, there is illustrated in FIG. 1 an embodiment, generally indicated 20, of an apparatus shown operatively positioned across the head of a patient P for supporting a nasal cannula 22 across the face of the patient for delivery of oxygen from a source to the patient's nostrils by way of the cannula 22. The nasal cannula 22 includes two branches 30, 32 positionable on opposite sides of a patient's head and a central portion 26 joining the branches together and including nostril orifices 28. Typically, the branches 30, 32 are sufficiently sized (i.e. in length) so as to be capable of being draped across the ears of the patient for supporting the nostril orifices 28 in operative registry with the patient's nostrils. As will be apparent herein, each branch 30 or 32 is adhesively connected to a corresponding portion of the apparatus 20 so that the branches 30 and 32 are supported on opposite sides of the patient's head and in spaced relationship with the patient's ears.

With reference to FIGS. 1-4, the apparatus 20 includes means, generally indicated 36, providing a soft, flexible strap positionable across the head of the patient P and including two opposite end portions 38 and 40 to which the branches 30 and 32 of the cannula 22 are adhesively securable. The width of the strap means 36 is relatively small (e.g. about 0.8 inches), and the length of the strap means 36 is sized (e.g. about 12.5 inches) so that when draped across the top of the patient's head in a side-to-side orientation, each end portion 38 or 40 is disposed adjacent a corresponding ear of the patient. The strap means 36 includes a foundation strip 52 and layup arrangements, described herein, of superposed strips attached to the foundation strip 52. The foundation strip 52 extends the entire length of the strap means 36 and terminates at opposite ends 54, 56 of the strap means 36. Although the material of the foundation strip 52 may be comprised of any of a number of suitable materials, the foundation strip 52 of the depicted embodiment 20 includes a strip of laminated spunbond polypropylene including a lower (as viewed in FIGS. 3 and 4) layer 42 of spunbond polypropylene and an upper (laminate) layer 44 of thin (e.g. 1.0 mil thick) polyethylene film. As will be apparent herein, the spunbond polypropylene provides the underside of the foundation strip 52 with a relatively soft surface for engaging the head of the patient P. A laminated spunbond polypropylene material found to be well-suited for use as the foundation strip 52 is available from Poly-bond, Inc. of Waynesboro, Va.

Associated with each end portion 38 or 40 of the strap means 36 is a layup arrangement 60 of superposed strips of elongated form which facilitate the adhesive joinder of the end portions 38, 40 to the branches 30, 32 of the nasal cannula 22. As best shown in FIG. 3, each layup arrangement 60 includes a first piece 62 of double-sided tape, a piece 64 of release tape, a second piece 66 of double-sided tape, a first (long) piece 68 of soft material such as spunbond polypropylene, and a second (shorter) piece 70 of material such as spunbond polypropylene.

The first piece 62 of double-sided tape has a lower (as viewed in FIG. 3) adhesive-bearing surface which is adhesively joined to the upper surface of the laminate layer 44 of the foundation strip 52 and extends along the corresponding end portion 38 or 40 from the end 54 or 56 for a short distance therealong. On the other hand, the piece 64 of release tape has a lower adhesive-bearing surface and an opposite adhesive-free upper surface and is positioned adhesive-side down over the foundation strip 52 so that the piece covers a portion of the double-sided tape piece 62 and a portion of the laminate layer 44 of the foundation strip 52, as best shown in FIG. 4. A double-backed tape found to be well-suited for use as the piece 62 is available from 3M Company of St Paul, Minn. under the trade designation 9877. A release tape found to be well-suited for use as the release tape piece 64 is also available from 3M Company under the trade designation 9921.

The second piece 66 of double-sided tape is positioned in the layup arrangement 60 so that the lower (as viewed in FIG. 3) of its adhesive-bearing faces overlies the upper adhesive-bearing side of the first double-sided tape piece 62 and the upper (non-adhesive-bearing) face of the release tape piece 64. The regions of contact between the adhesive-bearing faces of the tape pieces 62 and 66 securely join the pieces 62 and 66 to one another in these regions of contact, while the adhesive-free upper face of the release tape piece 64 permit the portion of the tape piece 66 in contact therewith to be manually peeled back from the upper face of the release tape piece 64. As will be apparent herein, the adhesive borne on the lower (as viewed in FIG. 3) adhesive-bearing face of the double-sided tape piece 66 provides an adhesive amount, indicated 45, with which each end portions 38 and 40 of the strap means 36 is adhesively secured to the corresponding branch 30 or 32 of the cannula 22. The length of the double-sided tape piece 66 corresponds generally to that of the combined length of the tape piece 62 and release tape piece 64 shown in the overlapped condition illustrated in FIG. 3.

To facilitate the removal, or peeling back, of the tape piece 66 from the adhesive-free upper face of the release tape piece 64, the shorter piece 70 comprised, for example, of the aforementioned spunbond polypropylene, is adhesively secured to a tip section, indicated 88, of the lower adhesive-bearing face of the tape piece 66 so that an end section, indicated 86, extends outboard of (or beyond) the corresponding end of the tape piece 66. The shorter piece 70 is securely adhered to the tape piece 66 by way of the adhesive borne by the lower face of the tape piece 66. It follows that since the lower (as viewed in FIG. 3) face of the shorter piece 70 does not securely adhere to the adhesive-free face of the release tape piece 64 or to the laminate layer 44 of the foundation strip 52, the end section 86 of the shorter piece 70 is free to be grasped between the fingers of a user for the purpose of peeling the tape piece 66 back from the release tape 64 in the direction of the corresponding arrow 82 or 84 of FIG. 4.

The long piece 68 of material, such as the aforementioned spunbond polypropylene, is adhesively secured along the upper (as viewed in FIG. 3) adhesive-bearing side of the double-sided piece 66 to provide the top of the layup arrangement 60 with a relatively soft surface. The length of the piece 68 generally corresponds with that of the double-sided tape piece 66 so that the adhesive borne by the upper side thereof is entirely covered by the piece 68.

With reference still to FIGS. 3 and 4, the apparatus 20 also includes adjustment means, generally indicated 92, associated with the strap means 36 with which the length of the strap means 36 can be adjusted. Since a feature of the apparatus embodiment 20 relates to its capacity to support the branches 30, 32 of the cannula 22 in a spaced relationship above the patient's ears, the adjustment means 92 enables the length of the strap means 36 (as measured between the end portions 38, 40) to be altered so that a single apparatus 20 can be used to support a nasal cannula 22 comfortably upon a patient having a head within a range of different head sizes.

In the depicted embodiment, the adjustment means 92 includes a piece 96 of double-sided tape (such as is available from 3M Company under the trade designation 1509) having an upper (as viewed in FIGS. 3 and 4) adhesive-bearing side which is overlain with a strip 94 of vinyl (or another suitable film) having a length which generally corresponds with that of the double-sided tape piece 96 so that the adhesive borne by the upper side thereof is entirely covered by the piece 94. Furthermore, the adjustment means 92 is joined to the foundation strip 52 in a manner similar to the manner in which the double-backed tape piece 66 is joined to an end section of the foundation strip 52. To this end, a layup arrangement 97 (FIG. 3) comprised of a piece 98 of double-backed tape is secured atop the laminate film layer 44 of the foundation strip 52 and a piece 100 of release tape is secured adhesive-side down upon an end section of the tape piece 98, as shown in FIG. 4. One end section of the lower adhesive-bearing face of the tape piece 96 is, in turn, positioned upon the overlapping arrangement 97 comprised of the tape piece 96 and release tape piece 100.

As will be apparent herein, the sections of the adhesive-bearing faces of the tape pieces 96 and 98 which are in contact with one another are adhesively bonded to one another in a manner which prevents the tape 96 from being peeled from the tape piece 98 in these regions of contact. An example of a tape found to be well-suited for use as the double-sided tape piece 98 is the aforementioned 9877 tape available from the 3M Company, and a release tape found to be well-suited for use as the release tape piece 100 is the aforementioned 9921 release tape available from the 3M Company.

Although the adhesive borne by the lower (as shown in FIG. 4) face of the double-backed tape piece 96 is sticky to the touch, it does not possess sufficient strength to prevent the rightwardmost end (as shown in FIG. 4) of the tape piece 96 from being forcibly peeled from the adhesive-free top surface of the laminate layer 44 of the foundation strip 52 in the direction of the arrow 108 of FIG. 4.

To facilitate the removal, or peeling back, of the tape piece 96 from the adhesive-free upper faces of the laminate layer 44 of the foundation strip 52 and release tape piece 100, a short piece 104 comprised, for example, of the aforementioned spunbond polypropylene, is adhesively secured to a tip section, indicated 102 in FIG. 3, of the lower adhesive-bearing face of the tape piece 104 to prevent the tip section 102 from adhering to the laminate layer 44. This short piece 104 is securely adhered to the tape piece 96 by way of the adhesive borne by the lower face of the tape piece 96. It follows that since the lower (as viewed in FIG. 3) face of the short piece 104 does not adhere to the adhesive-free face of the laminate layer 44 of the foundation strip 52, the end of the tape piece 96 disposed opposite the tape piece 98 (and which is sandwiched between the vinyl strip 94 and the short piece 104) is free to be grasped between the fingers of a user for the purpose of peeling the tape piece 96 back from the surface of the laminate layer 44 in the direction of the arrow 108 in FIG. 4.

To use the apparatus 20 for the purpose of supporting the nasal cannula 22 across the face of a patient P and with reference to FIG. 5, each layup arrangement 60 is peeled back piece 70-end-first from the laminate layer 44 and release strip 64 (in the direction of the corresponding FIG. 4 arrow 82 or 84) to accommodate the sideways insertion of a corresponding branch 30 or 32 of the cannula 22 between the lower (as viewed in FIG. 3) of the adhesive-bearing face of the tape piece 66 and the release tape 64. It follows that as the tape piece 66 is peeled from the release tape 64, the adhesive securement between the regions of contact between the adhesive-bearing surfaces of the tape piece 62 and the tape piece 66 prevents the tape piece 66 from being completely removed from the remainder of the strap means 36 and is advantageous in this respect.

With the tape piece 66 peeled from the release tape 64 as aforedescribed, a branch 30 or 32 of the cannula 22 is inserted sideways within the spacing provided between the peeled-apart tape piece 66 and release tape 64 in the manner illustrated in FIG. 5, and then the tape piece 66 is positioned across the branch 30 or 32 and pressed onto the release tape 64 so that the branch 30 or 32 is adhesively secured to the end portion 38 or 40 of the strap means 36. With each branch 30 or 32 secured to a corresponding end portion 38 or 40 of the strap means 36, the strap means 36 is positioned across the top of the patient's head so that the branches 30, 32 are disposed on opposite sides of the patient's head.

In an instance in which the apparatus 20 cannot be placed across the top of a patient's head due, for example, to the existence of bandages positioned atop the patient's head, the apparatus 20 can be positioned across the back of the patient's head for securing the cannula branches 30, 32 against the opposite sides of the head. Therefore, although the apparatus embodiment 20 is described and shown herein as being positionable across the top of a patient's head, the phrase "across the head" in accordance with the broader aspects of the present invention is intended to encompass the disposition of the apparatus 20 across the back, as well as the top, of the head.

When securing the branches 30, 32 of the cannula 22 within the end portions 38 or 40 of the strap means 36 in accordance with the principles of the present invention, the strap means 36 may be positioned across the patient's head before the branches 30, 32 are secured (e.g. one-at-a-time) within the end portions 38, 40 of the strap means 36 or the branches 30, 32 may be secured (e.g. one-at-a-time) within the end portions 38, 40 of the strap means 36 before the strap means 36 are positioned across the patient's head. If, however, the cannula 22 is already positioned across the patient's face (and in registry with the patient's nostrils) before the apparatus 20 is attached thereto, it may be preferable to leave the cannula 22 in place and position the strap means 36 across the patient's head before securing the branches 30, 32 one-at-a-time to the end portion 38, 40 of the strap means 36.

To adjust the length of the strap means 36 so that each branch 30 or 32 is supported on opposite sides of the head and in a spaced relationship with the patient's ears and with reference to FIG. 6, the tape 96 of the adjustment means 92 is peeled piece 104-end-first from the laminate layer 44 (in the direction of the FIG. 4 arrow 108) to expose a substantial portion of the foundation strip 52 underlying the tape 96. The exposed portion of the foundation strip 52 is then pinched or otherwise moved to a folded condition as illustrated in FIG. 6 so that the end portions 38, 40 are thereby moved closer together and so that the end portions 38, 40 of the strap means 36 are positioned at a height alongside the patient's head at which the end portions 30, 32 and the cannula branches 38, 40 supported thereby are disposed in a spaced relationship above the patient's ears.

While the pinched portion, indicated 110 in FIG. 6, of the foundation strip 52 is maintained in its folded condition, the pinched portion 110 of the strip 52 is folded appropriately (adjacent the head) and positioned atop the remainder of the foundation strip 52 so as to extend therealong. The tape piece 96 of the adjustment means 92 is then replaced across the foundation strip 52 in the manner shown in FIG. 7 so that the pinched portion 110 of the foundation strip 52 is captured beneath the tape piece 96 and the remainder of the foundation strip 52 so as to preserve the folded condition of the pinched portion 110 and thereby preserve the spaced relationship of the end portions 38, 40 above the ears.

An advantage provided by the apparatus 20 relates to the fact that once the cannula branches 30, 32 are adhesively secured to the end portions 38, 40 of the strap means 36, the branches 30, 32 are prevented from shifting in a lengthwise direction relative to the end portions 38, 40. Thus, when the strap means 36 is positioned across the patient's head with the branches 30, 32 secured thereto, the likelihood that the branches 30, 32 will inadvertently shift relative to the end portions 38, 40 and thereby move out of registry with the patient's nostrils or increase the patient's discomfort when wearing the cannula 22 is appreciably reduced.

It will be understood that numerous modifications and substitutions can be had to the aforedescribed embodiments without departing from the spirit of the invention. For example, although the end portions 38, 40 of the strap means 36 of the aforedescribed embodiment 20 has been shown and described as including an adhesive-bearing layup arrangement 60 which cooperates with an underlying portion of the foundation strip 52 for adhesively securing the cannula branches 30, 32 to the end portions 38, 40 when opposing faces are pressed in engagement with one another, an apparatus in accordance with the present invention may include a continuous (i.e. one-piece) foundation strip having an adhesive-coated end portion capable of being folded back upon and secured to itself across a cannula branch to adhesively secure the cannula branch to an end portion of the apparatus. Accordingly, the aforedescribed embodiments are intended for the purpose of illustration and not as limitation.

I claim:

1. Apparatus for supporting a nasal cannula across the face of a patient for use wherein the nasal cannula includes two branches positionable on opposite sides of the patient's head when the cannula is used, the apparatus comprising:

strap means positionable across the head of a patient and including two opposite end portions which are disposed adjacent the ears of the patient when the strap means are positioned across the head as aforesaid; and an amount of adhesive borne by each end portion of the strap means for adhesively securing each branch of the nasal cannula to a corresponding end portion of the strap means so that by folding each end portion back upon itself and about a corresponding branch of the nasal cannula so that each branch of the nasal cannula is positioned between two opposing folded sections of the end portions of the strap means and then pressing the opposing folded sections of the end portions together so that each branch is adhesively secured to a corresponding end portion of the strap means and then positioning the strap means across the head of a patient as aforesaid, the branches of the nasal cannula are supported on opposite sides of the patient's head by the strap means, and wherein the amount of adhesive borne by each end portion of the strap means is disposed thereupon so that when the opposing folded sections of the end portions of the strap means are pressed together as aforesaid, the amount of adhesive borne by each end portion directly contacts both of its opposing folded sections and the surface of the nasal cannula branch to prevent slippage of the branch relative to the corresponding end portion; and wherein the apparatus further includes means associated with the strap means for adjusting the length of the strap means as measured between the end portions thereof.

2. The apparatus as defined in claim 1 wherein the strap means includes a foundation strip having two opposite ends which are positionable adjacent the patient's ears when the strap means are positioned across the patient's head, and the amount of adhesive borne by each end portion of the strap means is attached to the foundation strip adjacent each end thereof.

3. The apparatus as defined in claim 2 wherein the strap means includes a piece of adhesive-bearing tape secured to the foundation strip adjacent at least one end thereof, and the amount of adhesive borne by the at least one end portion of the strap means is provided by the adhesive borne by the piece of adhesive-bearing tape.

4. The apparatus as defined in claim 2 wherein the strap means includes a piece of double-sided tape having two adhesive-bearing faces, the piece of double-sided tape is adhesively secured to the foundation strip adjacent one end thereof by way of the adhesive borne by one of the adhesive-bearing faces of the tape piece, and the adhesive borne by the other of the adhesive-bearing faces of the tape piece is adapted to engage a corresponding branch of the cannula for securing the corresponding cannula branch to the strap means.

5. The apparatus as defined in claim 1 wherein the strap means includes means providing a release surface against which the adhesive amount is positioned until the adhesive amount and the release surface are separated from one another for purposes of securing a cannula branch to the strap means.

6. The apparatus as defined in claim 1 wherein the adjusting means includes an elongated strip having two ends wherein one of the ends of the elongated strip is secured to the strap means along the length thereof at one location between the end portions thereof and the other end of the elongated strip is securable to the strap means at another location along the length thereof so that by arranging a section of the strap means disposed between the end portions thereof in a folded condition and securing said another end of the elongated strip to the strap means and across the folded section, the elongated strip maintains the folded section in a folded condition and thereby alters the length of the strap means as measured between the end portions of the strap means.

7. The apparatus as defined in claim 6 wherein the elongated strip is a strip of adhesive-bearing tape having one end which is secured to the strap means at said one location thereof and another end which is secured to the strap means at said another location thereof.

8. The apparatus as defined in claim 1 wherein the adjusting means includes an elongated strip, the elongated strip is adhesively securable to the strap means, and the strap means includes a foldable section disposed between the end portions thereof which is capable of being arranged in a folded condition so that by arranging said foldable section in a folded condition and adhesively securing the elongated strip to the strap means across the foldable section, the length of the strap means as measured between the end portions of the strap means is altered.

9. Apparatus as defined in claim 1 in combination with a nasal cannula.

10. A method for supporting a nasal cannula across the face of a patient for use wherein the nasal cannula includes two branches positionable on opposite sides of the patient's head when the cannula is used, the method comprising the steps of:

providing strap means positionable across the head of a patient wherein the strap means includes two opposite end portions which are disposed adjacent the ears of the patient when the strap means is positioned across the head as aforesaid and wherein an amount of adhesive is borne by each end portion of the strap means; and adhesively securing each branch of the nasal cannula to a corresponding end portion of the strap means by folding the corresponding branch of the nasal cannula so that each branch of the nasal cannula is positioned between a corresponding set of two opposing folded sections of the end portions of the strap means and then pressing the opposing folded sections of the end portions together so that amount of adhesive borne by each end portion of the strap means directly contacts both of the opposing folded sections of the corresponding end portion and the surface of the nasal cannula branch so that adhesively securing each branch of the cannula to a corresponding end portion of the strap means as aforesaid and positioning the strap means across the head of a patient, the branches of the nasal cannula are supported on opposite sides of the patient's head by the strap means and each nasal cannula branch is prevented from slipping relative to the corresponding end portion of the strap means to which it is secured;

arranging a section of the strap disposed between the end portions thereof in a folded conditions; and securing said section of the strap means in the folded condition to thereby alter the length of the strap means as measured between the end portions thereof.

11. Apparatus for supporting a nasal cannula across the face of a patient for use wherein the nasal cannula includes two branches positionable on opposite sides of the patient's head when the cannula is used, the apparatus comprising:

strap means positionable across the head of a patient and including two opposite end portions which are disposed adjacent the ears of the patient when the strap means are positioned across the head as aforesaid;

an amount of adhesive borne by each end portion of the strap means for adhesively securing each branch of the nasal cannula to a corresponding end portion of the strap means so that by adhesively securing each branch to a corresponding end portion of the strap means and positioning the strap means across the head of a patient as aforesaid, the branches of the nasal cannula are supported on opposite sides of the patient's head by the strap means; and means associated with the strap means for adjusting the length of the strap means as measured between the end portions thereof.

12. The apparatus as defined in claim 11 wherein the adjusting means includes an elongated strip having two ends wherein one of the ends of the elongated strip is secured to the strap means along the length thereof at one location between the end portions thereof and the other end of the elongated strip is securable to the strap means at another location along the length thereof so that by arranging a section of the strap means disposed between the end portions thereof in a folded condition and securing said another end of the elongated strip to the strap means and across the folded section, the elongated strip maintains the folded section in a folded condition and thereby alters the length of the strap means as measured between the end portions of the strap means.

13. The apparatus as defined in claim 12 wherein the elongated strip is a strip of adhesive-bearing tape having one end which is secured to the strap means at said one location thereof and another end which is secured to the strap means at said another location thereof.

14. The apparatus as defined in claim 11 wherein the adjusting means includes an elongated strip, the elongated strip is adhesively securable to the strap means, and the strap means includes a foldable section disposed between the end portions thereof which is capable of being arranged in a folded condition so that by arranging said foldable section in a folded condition and adhesively securing the elongated strip to the strap means across the foldable section, the length of the strap means as measured between the end portions of the strap means is altered.

15. Apparatus for supporting a nasal cannula across the face of a patient for use wherein the nasal cannula includes two branches positionable on opposite sides of the patient's head when the cannula is used, the apparatus comprising:

strap means positionable across the top of the head of a patient and including two opposite end portions which are disposed adjacent the ears of the patient when the strap means are positioned across the head as aforesaid;

at least one end portion of the strap means includes opposing surfaces wherein at least one of the opposing surfaces bears an amount of adhesive and the opposing surfaces are adhesively securable to one another by way of the adhesive when pressed against one another so that by positioning a corresponding branch of the nasal cannula between the opposing surfaces and then pressing the opposing surfaces against one another, the adhesive borne by the at least one of the opposing surfaces adhesively secures the cannula branch between the opposing surfaces and thereby secures the cannula branch to said one end portion of the strap means;

means associated with the strap means for adjusting the length of the strap means as measured between the end portions thereof wherein the strap means includes a mid-section disposed between the end portions of the strap means, and the adjusting means includes a piece of tape associated with the strap means for adhesively securing the mid-section of the strap means in one of a number of alternative folded conditions so that the length of the strap means as measured between the end portions thereof is altered.

16. A method for supporting a nasal cannula across the face of a patient for use wherein the nasal cannula includes two branches positionable on opposite sides of the patient's head when the cannula is used, the method comprising the steps of:

providing strap means positionable across the head of a patient wherein the strap means includes two opposite end portions which are disposed adjacent the ears of the patient when the strap means is positioned across the head as aforesaid; and adhesively securing each branch of the nasal cannula to a corresponding end portion of the strap means so that by adhesively securing each branch to a corresponding end portion of the strap means and positioning the strap means across the head of a patient, the branches of the nasal cannula are supported on opposite sides of the patient's head by the strap means;

arranging a section of the strap disposed between the end portions thereof in a folded condition; and securing said section of the strap means in the folded condition to thereby alter the length of the strap means as measured between the end portions thereof.

* * * * *

UNITED STATES PATENT AND TRADEMARK OFFICE
CERTIFICATE OF CORRECTION

PATENT NO. : 5,704,916
DATED : January 6, 1998
INVENTOR(S) : Timothy N. Byrd

It is certified that error appears in the above-indentified patent and that said Letters Patent is hereby corrected as shown below:

Column 8, line 67 (the last line in the column), between "ing the" and "corresponding branch" should appear the following:

--corresponding end portion back upon itself and about a--.

Signed and Sealed this

Third Day of March, 1998

Attest:

BRUCE LEHMAN

Attesting Officer

Commissioner of Patents and Trademarks